United States Patent
Butler

(10) Patent No.: US 6,732,962 B1
(45) Date of Patent: May 11, 2004

(54) WASTE TREATMENT APPARATUS

(75) Inventor: Mark H. Butler, Carlton (AU)

(73) Assignee: Medivac Technology Pty Limited, Carlton (AU)

( * ) Notice: Subject to any disclaimer, the term of this patent is extended or adjusted under 35 U.S.C. 154(b) by 0 days.

(21) Appl. No.: 09/869,180

(22) PCT Filed: Dec. 24, 1999

(86) PCT No.: PCT/AU99/01159

§ 371 (c)(1),
(2), (4) Date: Nov. 2, 2001

(87) PCT Pub. No.: WO00/38744

PCT Pub. Date: Jul. 6, 2000

(30) Foreign Application Priority Data

Dec. 24, 1998 (AU) .............................. PP 7946

(51) Int. Cl.$^7$ .............................. B02C 19/12
(52) U.S. Cl. .............. 241/57; 241/65; 241/235; 241/285.2; 241/606
(58) Field of Search .............. 241/18, 23, 27, 241/280, 281, 606, 57, 236, 235, 285.2, 65, 285.3

(56) References Cited

U.S. PATENT DOCUMENTS

| 4,578,185 A | * | 3/1986 | Wilson et al. .............. 241/606 |
| 4,884,756 A | * | 12/1989 | Pearson ..................... 241/42 |
| 5,048,766 A | * | 9/1991 | Gaylor et al. ................ 241/65 |
| 5,089,228 A | * | 2/1992 | Meijer ........................ 241/606 |
| 5,251,825 A | * | 10/1993 | Dumaine et al. .............. 241/16 |
| 5,424,033 A | | 6/1995 | Roland |
| 5,614,157 A | * | 3/1997 | Hall ........................... 241/606 |
| 5,720,438 A | * | 2/1998 | Devine et al. ................ 241/21 |
| 5,799,883 A | * | 9/1998 | Lewis et al. ................. 241/21 |
| 5,979,804 A | * | 11/1999 | Abrams et al. ............... 241/15 |

FOREIGN PATENT DOCUMENTS

| EP | 0597779 | 5/1994 |
| EP | 0763390 | 3/1997 |
| FR | 2704758 | 11/1994 |
| FR | 2715851 | 8/1995 |
| WO | WO95/32063 | 11/1995 |

* cited by examiner

*Primary Examiner*—Mark Rosenbaum
(74) *Attorney, Agent, or Firm*—Collen IP; Donald J. Ranft

(57) ABSTRACT

A waste treatment device includes a sealable chamber having an inlet for receiving waste to be treated and an outlet through which the treated waste is discharged. A cutting mechanism within the sealable chamber shreds the waste and delivers the shredded waste to the chamber outlet. The cutting mechanism includes a planetary gearbox carrying two or more rotating cutting heads which are in close proximity to one another.

16 Claims, 5 Drawing Sheets

WASTE TREATMENT APPARATUS

FIELD OF INVENTION

The present invention relates to waste treatment apparatus and more particularly to waste treatment apparatus for use in the sterilisation of infectious and/or quarantined waste. However, it will be appreciated that the invention is not limited to that particular use and will find application in treating other types of waste which require sterilisation.

BACKGROUND

Hospitals produce a large amount of infectious and/or quarantined waste. Generally, most hospitals have a number of infectious waste collection bins dispersed throughout the various wards and departments. These waste bins are periodically collected and removed to an off-site waste treatment facility for chemical sterilisation or high-temperature incineration of the waste, followed by sterilisation of the bin itself. This is an expensive process which suffers from many disadvantages.

One such disadvantage is the risk of environmental damage during the transport of infectious waste over public roads. In addition, the building and operation of an off-site chemical or incineration treatment centre represents a high capital cost outlay and requires expensive chemicals and/or fuels for operation.

OBJECTS AND SUMMARY OF THE INVENTION

It is an object of the present invention, at least in its preferred embodiment, to overcome or at least ameliorate one or more of the above prior art disadvantages.

Accordingly to one aspect of the invention there is provided a waste treatment apparatus comprising:
  a first sealable chamber for containing untreated waste, the chamber having therein a cutting mechanism and vents through which steam may be introduced under pressure.

In other preferred embodiment, the device further comprises a grate adjacent to the cutting mechanism through which treated waste is ejected from the first chamber.

In another embodiment of the invention, the first chamber further includes an advance mechanism for urging the waste against the cutting mechanism.

In other embodiments there is provided a pivoting hopper for depositing untreated waste into the first chamber. There is concurrently provided a transport for inverting a bin over the hopper.

In some embodiments there is also provided a bin cleaning mechanism located beneath the hopper.

In some preferred embodiments a second sealable chamber in which waste deposited from the first chamber is treated.

In other embodiments of the invention, a third chamber is interposed between the first and second chambers and comprises an isolation gate valve for separating the first and second chambers.

In other embodiments of the invention, either the first or the second chambers are provided with external jackets carrying steam to heat the respective chambers.

There is also disclosed means for collecting both the liquid and vapour discharges of the treatment chambers.

In particular embodiments, the cutting mechanism comprises a gearbox carrying two or more rotating cutting heads.

In some preferred embodiments, the gearbox is a planetary gearbox and the gearbox rotates within the first chamber.

In one form of the invention, the apparatus is mounted on the back of a truck or trailer to facilitate transporting from site to site. The truck or trailer can supply all the power requirements of the device, including electric, hydraulic, gas and/or pressurised steam.

In another form of the invention, the apparatus is produced as an on-site plant.

According to another aspect of the invention there is provide a method of treating waste comprising the steps of:
  (i) introducing untreated waste into a sealable chamber,
  (ii) shredding the waste in the chamber and simultaneously applying steam to the waste to thereby sterilise the waste, and
  (iii) discharging the shredded, sterilised waste from the chamber.

In some preferred methods of the invention, the shredded, sterilised waste is discharged into a second sealable chamber where the waste is subjected to further treatment.

In preferred embodiments of the invention, the waste in the second chamber is subjected to further steam treatment.

In other preferred embodiments of the invention, the method further comprises the steps of collecting liquid waste discharged during the process and sterilising it separately prior to disposal.

In one embodiment, the method also includes evacuating all air and/or gas from the chamber prior to steps (ii) and (iii) and decontaminated through a multi-stage active carbon filter or the like.

DETAILED DESCRIPTION OF THE INVENTION

Figure 1:
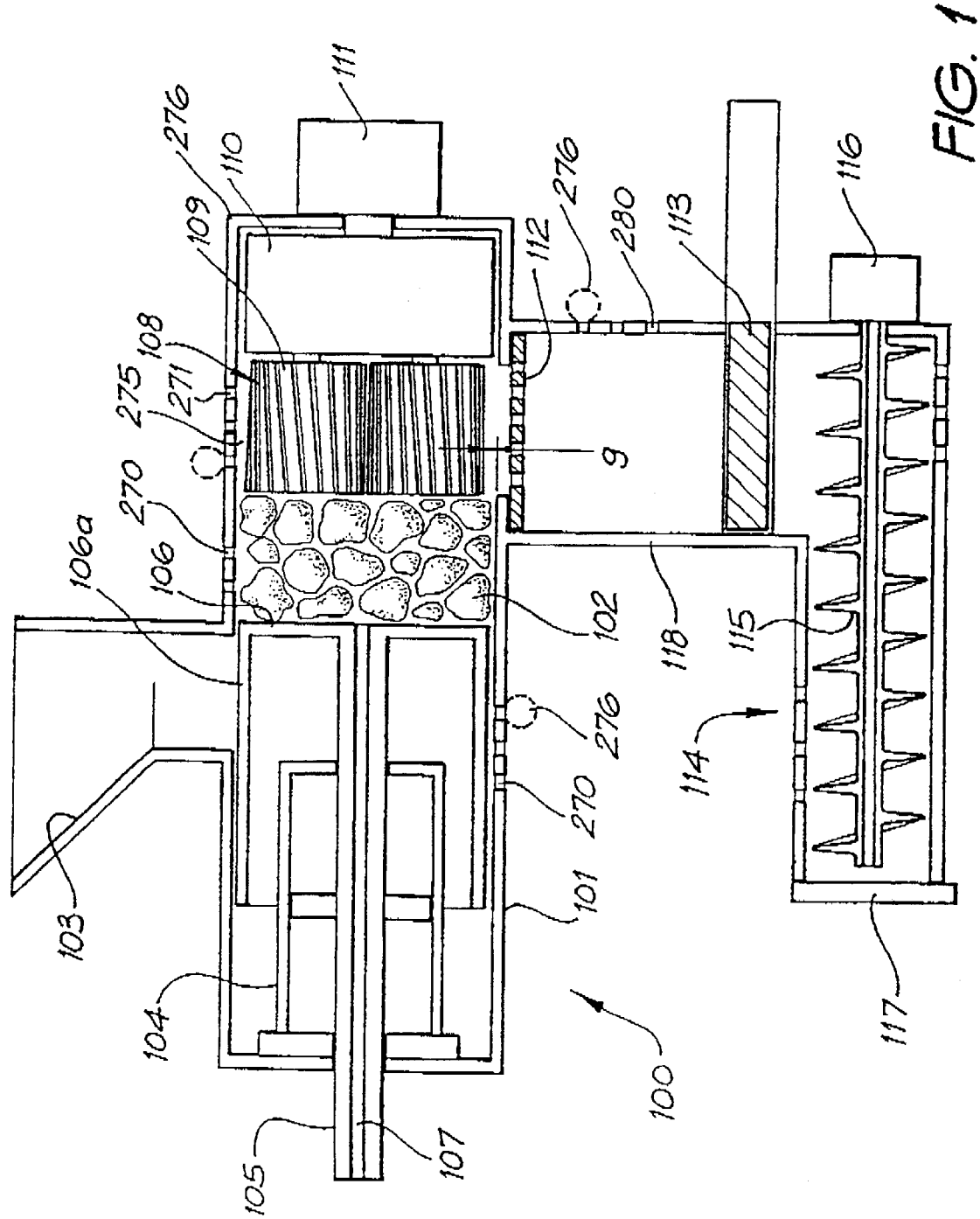
FIG. 1 is a schematic side view of a waste treatment device according to a first embodiment of the invention.

As shown in FIG. 1 an on-site waste treatment apparatus 100 includes a primary treatment chamber 101 into which waste 102 is fed through a chute 103 The primary chamber 101 includes an advance mechanism in the form of, for example, a hydraulic ram 104. The shaft of the ram 105 may include a central bore 107 through which steam is fed. The steam emerges through the head of the ram 106. The head 106 includes an elongated skirt 106a which serves to seal the chamber 101 from the chute 103 when the ram is sufficiently advanced.

After waste is introduced into the chamber, it may be sealed and evacuated prior to any introduction of steam to promote uniform penetration of steam into the mass of waste 102.

Owing to the action of the ram, waste matter 102 is forced under pressure against a shredding or cutting mechanism 108 located within the primary chamber 101. The cutting mechanism includes a hydraulic motor 111 which drives a planetary gear box 110, the planet gears of which are coupled to two or more rotating cutting heads 109.

Pressurised or super-heated steam ("steam") may be provided directly into the chamber 101 before and during the operation of the cutting mechanism in various ways. Additionally steam may be piped or otherwise provided to the chamber, either by vents 270 along the length of the chamber or by vents 271 in the area of the cutting heads 109. These vents, like others depicted in these examples are supplied by jackets or pipes 276 suggested in FIG. 1, but not shown for clarity.

In preferred embodiments of the invention, the temperature is monitored in the chamber 101 overtime. Waste is maintained in the chamber 101 at a specified temperature, for a specified time before the advance mechanism, and cutting mechanism 109 are activated. This may be done with automated process control equipment.

Waste material 102 which is forced by the ram into contact with the cutting heads 109 is thoroughly macerated and ejected from the chamber 101 through a grate 112 when the cycle is completed. The entire process may be auto recorded for record keeping purposes. The grate is replaceable and interchangeable with other grates so that the size of the grate openings can be varied to suit different types of waste or replaced for maintenance purposes. The narrow gap "g" between the cutting heads and the interior o the chamber helps control the site of the ejector.

Figure 2:
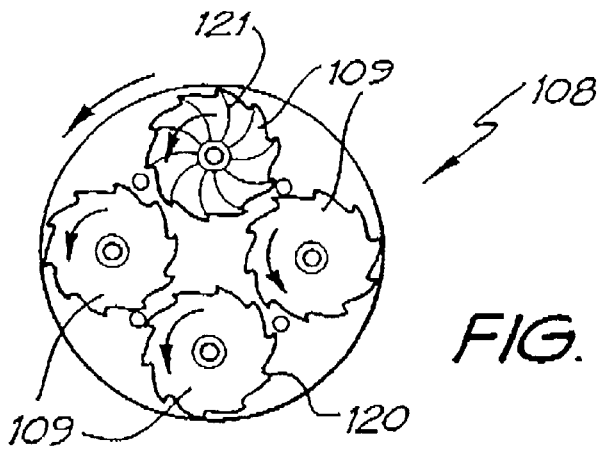
FIG. 2 is a front elevational view of the cutting head depicted in FIG. 1.
Figure 3:
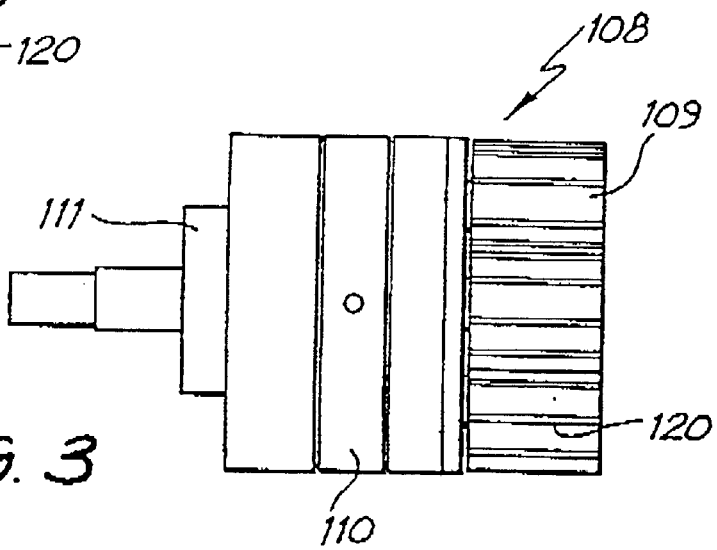
FIG. 3 is a side elevational view of the cutting head and gear box of the device shown in FIG. 2.
Figure 4:
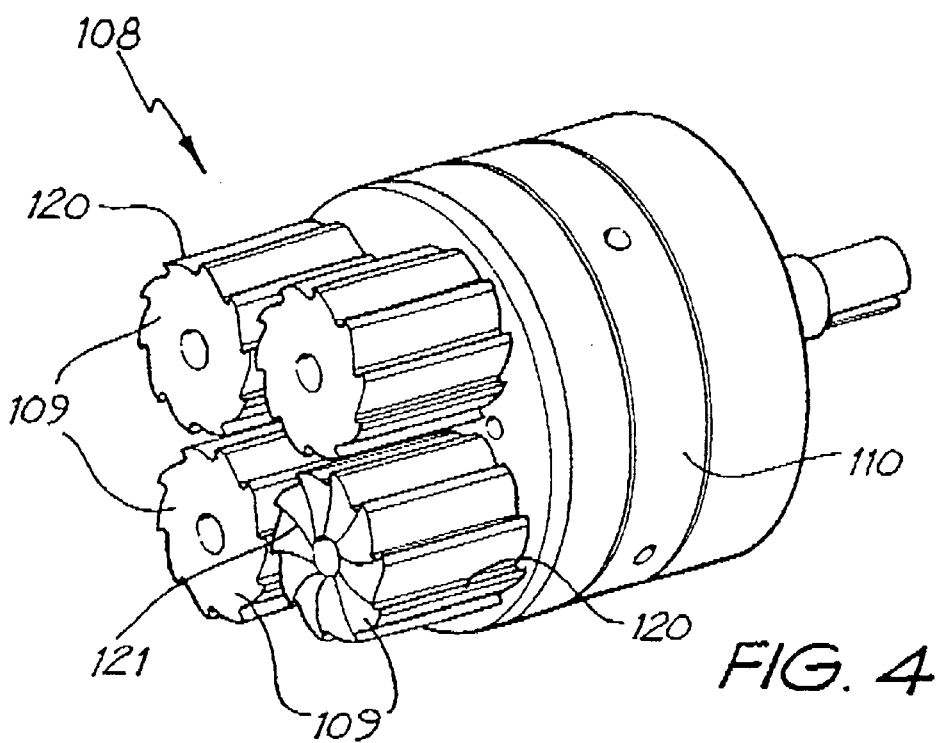
FIG. 4 is a perspective view of the cutting head and gear box of the device shown in FIG. 2.

The shredding mechanism 108 is shown in greater detail in FIGS. 2 to 4. As shown in these Figs., the cutting heads 109 are mounted on the shafts of the rotating planet gears of a planetary gear box 110. They are disposed around the gear box so that the clearance between the outside diameter of the cutting circle of the heads 109 and the inside diameter of the primary chamber 101 creates a narrow gap which limits the size of the waste which is ejected through the grate 112. The preferred number of cutting heads 109 is between two and four although more cutting heads 109 may be mounted on an appropriately designed planetary gear box, as required. Each of the cutting heads 109 is fashioned from a hardened steel to provide maximum durability and service life. Each cutting head 109 includes cutting edges 120 which run the full length of each head 109. A cutting head 109 may also include cutting edges 121 on a face or a portion of the face of the head 109. A small clearance is provided between adjacent heads. Owing to the action of the planetary gear box, the gear box itself 110 rotates in the same direction as the cutting heads but at a different speed to the cutters 109.

The clearance 275 between the chamber wall 276 an the cutting head 109 is kept small so that the waste is broken down by the heads 109 into small pieces. Waste leaving the primary chamber 101 enters an optional secondary processing chamber 118. Additional steam can be provided by vents 280 into this secondary chamber 118 which is sealable with a isolation gate valve 113 located beneath the grating 112. Shredded and steamed waste collects on the gate valve 113 after it passes through the grate 112. The grate valve is kept closed during the secondary steaming process and is opened after the secondary steaming process has been completed.

A discharge chamber 114 is located directly beneath the isolation gate valve 113 and receives the shredded and steam treated waste when the gate valve 113 is opened. Within the discharge chamber 114 there is an agitator or auger 115 that is driven by a motor 116 to tumble the waste which is again steamed during this step of the process which takes places as the primary main process is being repeated on the next batch of waste in the primary chamber 102 with the gate valve 113 closed.

The tertiary process in the discharge chamber 114 ensures that the waste material is thoroughly treated. When this cycle is complete, the discharge door 117 is opened and the shredded and sterilised material is ejected by the agitator 115 into a waste container for disposal.

Figure 5:
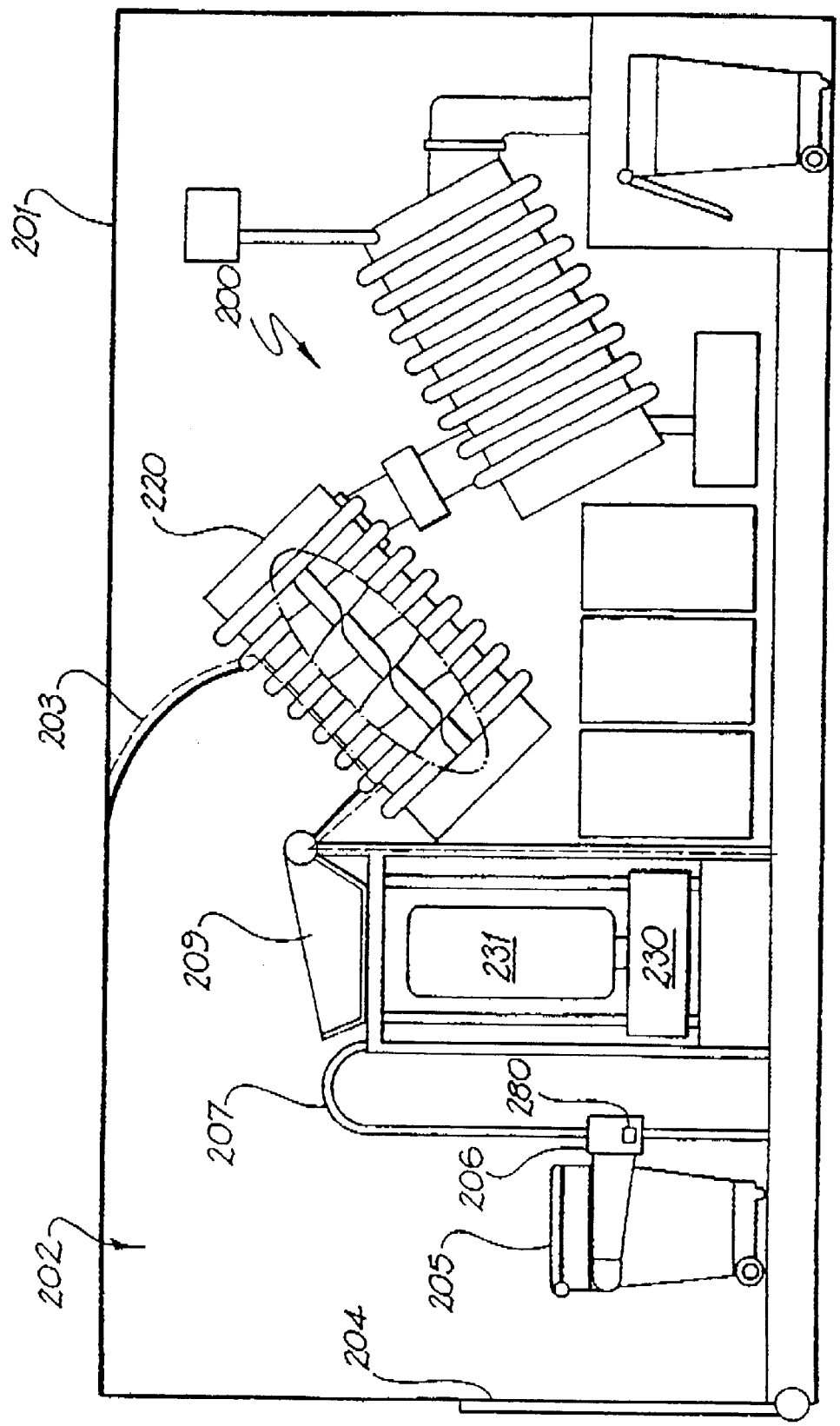
FIG. 5 is a schematic side view of a waste treatment device according to a second embodiment of the invention.
Figure 6:
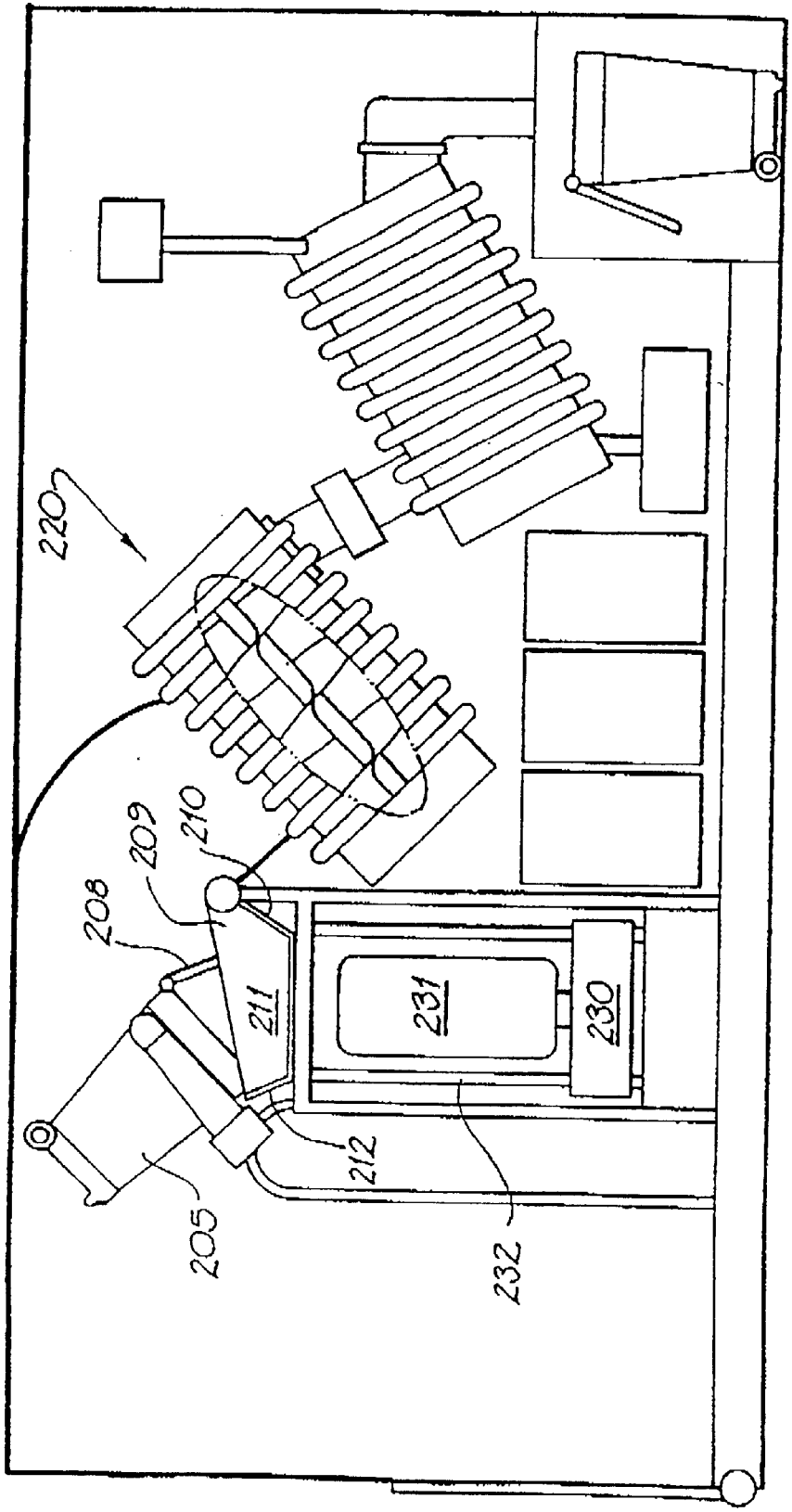
FIG. 6 is a view similar to FIG. 5 showing the waste being loaded.
Figure 7:
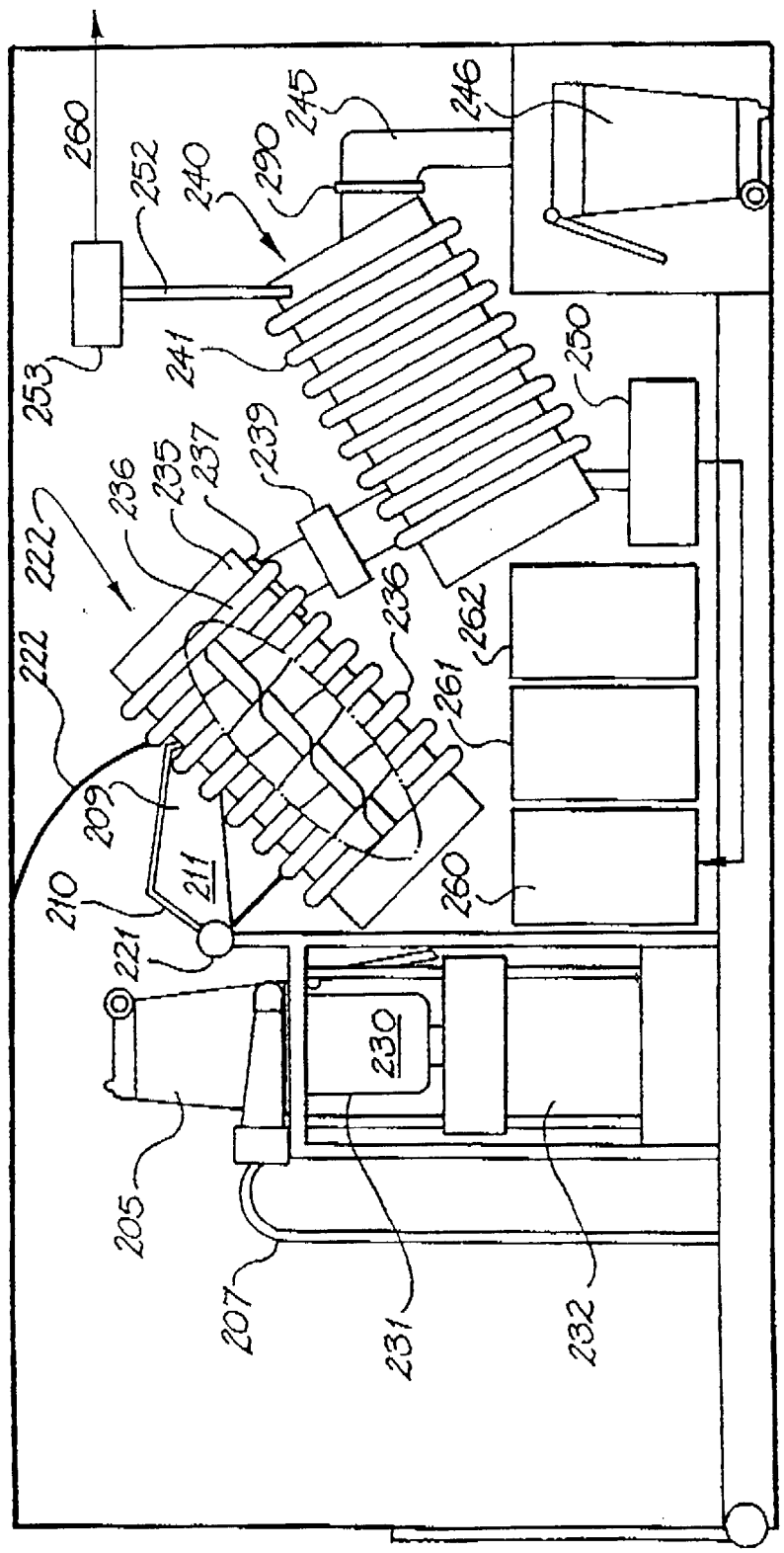
FIG. 7 is a view similar to FIG. 5 showing the waste material having been introduced into a first treatment chamber and the waste bin being cleaned.

Another embodiment of the invention which may utilise the same cutting mechanism 108 is shown in FIGS. 5 to 7. This waste treatment device 200 includes an optional sealed enclosure or housing 201 that includes a sealed loading chamber 202 which is partitioned (dotted lines 203) from the remainder of the device. The loading chamber 202 includes a sealable door 204 through which bins 205 may be introduced. The bins 205 are lifted and inverted by a gripper and arm 206 which follows a guide, rail or track 207. The gripper or arm may include a load cell 280 so that the weight of the bin 205 may be measured, recorded and accounted for.

The loading chamber has a bin cleaning device 230,231 which is mounted below a pivoting transfer hopper 209.

As shown in FIG. 6, once the bin 205 is inverted, the lid 208 opens allowing the waste contents of the bin 205 to fall into the hopper 209. To assist with the ejection of waste from the hopper, the hopper may be equipped with cavity walls 210 so that steam my be forced into the cavity and then into the working volume 211 of the hopper through vents (not shown) formed in the inner wall 212.

After the contents of the bin 205 have been discharged into the working volume 211 of the hopper, the bin is momentarily withdrawn or retracted along the guide 207 so that the hopper may deliver its contents to the primary processing chamber 220.

As shown in FIG. 7, the hopper 209 pivots around one edge 221 to deliver its contents into the primary processing chamber 220. The curved guide wall 222 assists in delivering the contents of the hopper into the processing chamber 220.

With the hopper 209 now pivoted out of the way, the inverted bin 205 can be advanced once again along the guide 207 into contact with a cleaning mechanism 230. The bin cleaning mechanism 230 comprises a rotating brush 231 which is raised along guide rails 232 into engagement with the bin 205. The rotating brush 231 may be assisted with the provision of steam, then lowered prior to the return of the hopper 209 to its original position as depicted in FIG. 5.

If required, the air from the loading chamber 202 may be evacuated after bin cleaning. The exhaust air is preferably drawn over a steam line to kill air-borne micro-organisms prior to venting to the atmosphere.

The primary processing chamber 220 comprises a generally cylindrical chamber 235 which can accommodate the entire contents of the hopper 209. The primary chamber 220 is analogous to and may be constructed similarly to the chamber 101 depicted in FIG. 1. It is sealed either with a separate door or by the action of a hydraulic ram. The chamber 235 may be evacuated prior to the introduction of steam. Waste material in the chamber 220 is then advanced either by a hydraulic ram or auger into contact with a cutting mechanism located at the top of the chamber 220 which mechanism is like the one depicted in FIGS. 2 to 4. External steam lines 236 may be provided along the length of the primary chamber so that steam may be delivered to its contents through vents located periodically along the jacket 236. Like the device depicted in FIG. 1, the embodiment depicted in FIG. 7 includes a grate 237 located near the cutting heads and a isolation valve 239 located between the primary chamber 220 and a tertiary processing chamber 240. Thus a secondary steam processing chamber is defined between the grate 237 and the isolation vale 239.

The tertiary processing chamber 240 may serve either or both of two distinct functions. One function of the secondary processing chamber is to further treat the shredded waste produced by the primary chamber 220 by treating it with additional steam provided through a steam jacket 241. In the alternative, the secondary processing chamber 240 may be used to dry the waste prior to discharge through heating of the auger blades internally with steam. The secondary chamber 240 is preferably provided with a ram, screw feeder or auger which moves the waste within the secondary chamber 240 toward a discharge chute 245 which discharges when the exit seal 290 is opened to a removable bin 246.

Both the first and third processing chambers 220, 240 may be provided with a facility for collecting the liquid runoff of the waste 250. In this way, accumulated liquids can be separated from the waste and treated, sterilised or vaporised separately, if required, prior to disposal.

Where the secondary chamber is used to dry waste, a vent 252 is provided to carry away water vapour and other vapours so that they can be treated, for example, with carbon filters 253 or other means of removing waste material from the vapour discharge.

Pressurised steam for the device 200 is provided by water held in a tank 260 which supplies its contents to a steam generator 261. The steam generator 261 derives its energy from a power source such as an LPG burner 262. The water tank 260 may be supplied with fresh water or water originating from the liquid trap 250 or vapour condensation and treatment device 253.

While the invention has been described with reference to particular details and methods of construction, these should be appreciated as having been provided by way of example and not as limitations to the scope or spirit of the invention.

What is claimed is:

1. A waste treatment device comprising:
   a first sealable chamber having an inlet for receiving waste to be treated; an outlet through which the treated waste is discharged, and vents through which steam may be introduced.
   a cutting mechanism within the first sealable chamber for shredding the waste in the first sealable chamber, the cutting mechanism comprising a planetary gearbox carrying two or more rotating cutting heads, the cutting heads being in close proximity to one another.

2. The device of claim 1, wherein the outlet has a removable grate adjacent to the cutting mechanism through which treated waste is discharged from the first chamber.

3. The device of claim 1, wherein:
   the first chamber further includes an advance mechanism for urging the waste against the cutting mechanism.

4. The device of claim 3, wherein:
   the advance mechanism is a hydraulic ram.

5. The device of claim 1 further comprising:
   a pivoting hopper for depositing untreated waste into the first chamber; and
   a transport for inverting a bin over the hopper.

6. The device of claim 5, wherein:
   a bin cleaning mechanism is located beneath the hopper;
   the hopper being pivotable to allow the cleaning mechanism to access an inverted bin held by the transport when the hopper has been pivoted out of the way.

7. The device of any of claims 1 to 6, wherein:
   the first chamber is provided with a means for venting, collecting and sterilising vapour discharged from the first chamber.

8. The device of claim 1, further comprising:
   a second sealable chamber in which waste deposited from the first chamber is treated.

9. The device of claim 8, wherein:
   the second chamber comprises an internal transport for displacing waste from an entry into the second chamber to a discharge.

10. The device of claim 8 wherein:
    the second chamber comprises a drying mechanism for removing water vapour from the waste in the second chamber.

11. The device of any of claims 8 to 10, wherein:
    the second chamber is provided with a means for venting, collecting and sterilising vapour discharged from the second chamber.

12. The device of claim 8, wherein:
    the second chamber comprises vents for introducing steam into the second chamber.

13. The device of 8, wherein:
    a third chamber is interposed between the first and second chambers and comprises an isolation gate valve for separating the first and second chambers.

14. The device of claim 13, wherein:
    the third chamber is provided with vents through which steam may be provided into the third chamber.

15. The device of claim 8, wherein:
    either of the first or second chambers are provided with external jackets carrying steam to heat the respective chambers.

16. The device of claim 1, wherein:
    the gearbox rotates within the first chamber.

* * * * *